US012623985B2

(12) United States Patent
Sadow et al.

(10) Patent No.: US 12,623,985 B2
(45) Date of Patent: May 12, 2026

(54) SELECTIVE TERMINAL CH ALUMINATION OF SATURATED HYDROCARBONS

(71) Applicants: IOWA STATE UNIVERSITY RESEARCH FOUNDATION, INC., Ames, IA (US); CORNELL UNIVERSITY, Ithaca, NY (US); UCHICAGO ARGONNE, LLC, Chicago, IL (US)

(72) Inventors: Aaron David Sadow, Ames, IA (US); Uddhav Kanbur, Ames, IA (US); Frederic A. Perras, Ames, IA (US); Alexander L. Paterson, Ames, IA (US); Andrew Kocen, Brooklyn, NY (US); Geoffrey W. Coates, Lansing, NY (US); Anne M. Lapointe, Ithaca, NY (US); Massimiliano Delferro, Chicago, IL (US); Ryan A. Hackler, Chicago, IL (US); Jessica Rodriguez, Ames, IA (US)

(73) Assignees: IOWA STATE UNIVERSITY RESEARCH FOUNDATION, INC., Ames, IA (US); CORNELL UNIVERSITY, Ithaca, NY (US); UCHICAGO ARGONNE, LLC, Chicago, IL (US)

( * ) Notice: Subject to any disclaimer, the term of this patent is extended or adjusted under 35 U.S.C. 154(b) by 713 days.

(21) Appl. No.: 17/983,165

(22) Filed: Nov. 8, 2022

(65) Prior Publication Data
US 2023/0219870 A1    Jul. 13, 2023

Related U.S. Application Data

(60) Provisional application No. 63/277,040, filed on Nov. 8, 2021.

(51) Int. Cl.
C07C 29/36    (2006.01)
B01J 2/12    (2006.01)
(Continued)

(52) U.S. Cl.
CPC .............. C07C 29/36 (2013.01); B01J 21/066 (2013.01); B01J 21/12 (2013.01); C07C 29/54 (2013.01); C07F 5/062 (2013.01); C07F 7/003 (2013.01)

(58) Field of Classification Search
CPC ......... C07C 29/26; C07C 29/50; C07C 17/06; C07C 41/01; C07C 45/55; C07C 51/15;
(Continued)

(56) References Cited

U.S. PATENT DOCUMENTS 3,894,066 A    7/1975 Buschhoff et al.
4,511,745 A *   4/1985 Bergman ................ C07C 17/00
570/252
(Continued)

OTHER PUBLICATIONS

Kretschmer, W. P., et al., An efficiet ytttrium catalysed versionof the "Aufbaureaktion" for the synthesis of terminal functionalised polyethylene, 39, pp. 6847-6852 (Year: 2010).*
(Continued)

*Primary Examiner* — Yate' K Cutliff
(74) *Attorney, Agent, or Firm* — Troutman Pepper Locke LLP (Rochester)

(57) ABSTRACT
Disclosed herein is the selective functionalization of one or more hydrocarbons ranging from the longest macromolecules to methane as the smallest. Functionalization is achieved through C—H activation of the one or more hydrocarbons and is carried out by the catalytic complex described herein. Also disclosed is the compound of formula (I) and the compound of formula (II).

27 Claims, 7 Drawing Sheets $$CH_4 + AlEt_3 \xrightarrow[-\text{Et-H}]{150\ ^\circ C,\ 12\ h} Al(CH_3)_x Et_{3-x}$$

(51) Int. Cl.
| | |
|---|---|
| *B01J 21/06* | (2006.01) |
| *B01J 21/12* | (2006.01) |
| *C07C 29/54* | (2006.01) |
| *C07F 5/06* | (2006.01) |
| *C07F 7/00* | (2006.01) |

(58) Field of Classification Search
CPC ... C07C 51/6724; C07C 231/02; C07C 29/54; B01J 21/12; B01J 21/00; B01J 27/125; C07F 5/062
See application file for complete search history.

(56) References Cited

U.S. PATENT DOCUMENTS

| | | | |
|---|---|---|---|
| 5,446,188 | A | 8/1995 | Gruber et al. |
| 6,171,475 | B1 | 1/2001 | Dufaud et al. |
| 6,451,937 | B1 * | 9/2002 | Hartwig ............... B01J 31/1608 556/11 |
| 8,048,394 | B2 | 11/2011 | Yano et al. |
| 8,415,267 | B2 | 4/2013 | Lee |
| 8,449,856 | B2 | 5/2013 | Yano et al. |
| 8,883,308 | B2 | 11/2014 | Polshettiwar et al. |
| 9,283,545 | B2 | 3/2016 | Asefa et al. |
| 9,533,286 | B2 | 1/2017 | Stamm Masias et al. |
| 9,943,826 | B2 | 4/2018 | Haynes et al. |
| 9,956,545 | B2 | 5/2018 | Calderone et al. |
| 10,351,781 | B2 | 7/2019 | Sinha et al. |
| 11,053,598 | B2 | 7/2021 | Chou |
| 11,198,112 | B2 | 12/2021 | Lu et al. |
| 11,857,951 | B2 | 1/2024 | Sadow et al. |
| 12,030,843 | B2 | 7/2024 | Sadow et al. |
| 12,151,230 | B2 | 11/2024 | Sadow et al. |
| 2006/0241327 | A1 * | 10/2006 | Periana ................ B01J 31/1805 702/22 |
| 2010/0056360 | A1 | 3/2010 | Lee |
| 2011/0250122 | A1 | 10/2011 | Joo et al. |
| 2011/0311635 | A1 | 12/2011 | Stucky et al. |
| 2012/0264599 | A1 | 10/2012 | Komatsu et al. |
| 2013/0318863 | A1 | 12/2013 | Chang et al. |
| 2018/0056277 | A1 | 3/2018 | Lee et al. |
| 2019/0126247 | A1 | 5/2019 | Deeba |
| 2019/0291092 | A1 | 9/2019 | Cargnello et al. |
| 2020/0122122 | A1 | 4/2020 | Gong et al. |
| 2021/0031176 | A1 | 2/2021 | Suriye et al. |
| 2021/0061971 | A1 | 3/2021 | Delferro et al. |
| 2021/0322961 | A1 | 10/2021 | Wattanakit et al. |
| 2022/0111356 | A1 | 4/2022 | Sadow et al. |
| 2022/0213007 | A1 | 7/2022 | Sadow et al. |
| 2024/0157338 | A1 | 5/2024 | Sadow et al. |
| 2025/0011477 | A1 | 1/2025 | Huang et al. |

OTHER PUBLICATIONS

Lyakin, O. Y., et al., Ni- and Pd-based homogeneous catalyst systems for direct oxygenation of C(sp3)-H groups, Applied Organometallic Chemistry, 37, pp. 1-27 (Year: 2022).*

Bae et al. "Catalytic Hydroxylation of Polypropylenes," J. Am. Chem. Soc. 127:767-776 (2005).

Bae et al., "Regiospecific Side-Chain Functionalization of Linear Low-Density Polyethylene with Polar Groups," Angew. Chem. Int. Ed. 44:6410-6413 (2005).

Kondo et al., "Rhodium-Catalyzed, Regiospecific Functionalization of Polyolefins in the Melt," J. Am. Chem. Soc. 124:1164-1165 (2002).

Bunescu et al., "Catalytic Hydroxylation of Polyethylenes," ACS Cent. Sci. 3:895-903 (2017).

Boaen et al., "Selective and Mild Oxyfunctionalization of Model Polyolefins," Macromolecules 36:7027-7034 (2003).

Chen et al., "Selective, Catalytic Oxidations of C-H Bonds in Polyethylenes Produce Functional Materials with Enhanced Adhesion," Chem. 7:137-145 (2021).

Diaz-Requejo et al., "Controlled, Copper-Catalyzed Functionalization of Polyolefins," Macromolecules 38:4966-4969 (2005).

Williamson et al., "Chemo- and Regioselective Functionalization of Isotactic Polypropylene: A Mechanistic and Structure-Property Study," J. Am. Chem. Soc. 141:12815-12823 (2019).

Williamson et al., "Regioselective C-H Xanthylation as a Platform for Polyolefin Functionalization," Angew. Chem. Int. Ed. 57:6261-6265 (2018).

Lewis et al., "Upcycling Aromatic Polymers through C-H Fluoroalkylation," Chem. Sci. 10:6270-6277 (2019).

Zhou et al., "Direct Amination of Polyethylene by Metal-Free Reaction," Macromolecules 50:3510-3515 (2017).

Plummer et al., "Mild Halogenation of Polyolefins Using an N-Haloamide Reagent," Polym. Chem. 9:1309-1317 (2018).

Kanbur et al., "Catalytic Carbon-Carbon Bond Cleavage and Carbon-Element Bond Formation Give New Life for Polyolefins as Biodegradable Surfactants," Chem. 7:1347-1362 (2021).

Hou et al., "Upcycling and Catalytic Degradation of Plastic Wastes, " Cell Reports Physical Science 2:1-30 (2021).

Jehanno et al., "Organocatalysis for Depolymerisation," Polymer Chemistry 10:172-186 (2019).

Lee et al., "Chemical Recycling of Plastic Waste via Thermocatalytic Routes," Journal of Cleaner Production 321:128989 12 pages (2021).

Cannavacciuolo et al., "A High-Throughput Approach to Repurposing Olefin Polymerization Catalysts for Polymer Upcycling," Angew. Chem. Int. Ed. 61:e202202258 (2022).

Gu et al., "Cp2ZrHCl Induced Catalytic Chain Scission of Diene-Based Polymers Under Mild Conditions: Influence of Chemical Environment Around C=C Bonds," Polymer 161:181-189 (2019).

Gu et al., "The Catalytic Cleavage of Carbon-Carbon Double Bond in Polychloroprene Induced by Schwartz's Reagent Via Chlorine Self-Assisted ß-alkyl Elimination Mechanism," Polymer 170:24-30 (2019).

Coates et al., "Chemical Recycling to Monomer for an Ideal, Circular Polymer Economy," Nature Reviews Materials 5:501-516 (2020).

Zhang et al., "Polyethylene Upcycling to Long-Chain Alkylaromatics by Tandem Hydrogenolysis/Aromatization," Science 370:437-441 (2020).

Office Action for U.S. Appl. No. 17/554,666 (Aug. 9, 2023).

U.S. Appl. No. 18/508,055, filed Nov. 13, 2023, first named inventor Aaron D. Sadow.

Xiao et al., "High-temperature-stable and Regenerable Catalysts: Pplatinum Nanoparticles in Aaligned Mesoporous Silica Wells," ChemSusChem. 6(10):1915-22 (2013).

Flaherty et al., "Metal-catalyzed C-C Bond Cleavage in Alkanes: Effects of Methyl Substitution on Transition-state Structures and Stability," J Am Chem Soc 136(27):9664-76 (2014).

Dufaud et al., "Catalytic Hydrogenolysis at Low Temperature and Pressure of Polyethylene and Polypropylene to Diesels or Lower Alkanes by a Zirconium Hydride Supported on Silica-Alumina: A Step Toward Polyolefin Degradation by the Microscopic Reverse of Ziegler-Natta Polymerization," Angew Chem Int Ed Engl 37(6):806-810 (1998).

Dong et al., "In Situ Quantitative Single-Molecule Study of Dynamic Catalytic Processes in Nanoconfinement," Nature Catalysis 1:135-140 (2018).

Celik et al., "Upcycling Single-Use Polyethylene into High-Quality Liquid Products," ACS Cent. Sci. 5:1795-1803 (2019).

Schmidt-Rohr and Spiess, "Chain Diffusion Between Crystalline and Amorphous Regions in Polyethylene Detected by 2D Exchange 13C NMR," Macromolecules 24:5288-5293 (1991).

Inoue et al., "Structural and Dynamical Studies of 13c-Labeled Polyethylene Adsorbed on the Surface of Silica Gel by High-Resolution Solid-State 13c Nmr Spectroscopy," Acta Polymer. 46:420-423 (1995).

Tennakoon et al., "Catalytic Upcycling of High-Density Polyethylene via a Processive Mechanism," Nat. Catal. 3:893-901 (2020).

Takei et al., "Anionic Surfactants: Lauric Products," JAOCS 62(2):341-347 (1985).

David B. Hatcher, "Fatty Alcohol Sulfates," The Journal of the American Oil Chemists' Society 34:175-178 (1957).

(56)                References Cited

OTHER PUBLICATIONS

Backstrom et al., "Trash to Treasure: Microwave-Assisted Conversion of Polyethylene to Functional Chemicals," Industrial & Engineering Chemistry Research 56:14814-14821 (2017).
Zheng et al., "Controlled Chain-Scission of Polybutadiene by the Schwarts Hydrozirconation," Chem. Eur. J. 19:541-548 (2013).
DOE Grant proposal (Jul. 1, 2020).
Office Action (Restriction) for U.S. Appl. No. 17/554,666 (Mar. 31, 2023).
Office Action for U.S. Appl. No. 17/497,206 (Mar. 2, 2023).
Wu et al., "Size-Controlled Nanoparticles Embedded in a Mesoporous Architecture Leading to Efficient and Selective Hydrogenolysis of Polyolefins," J. Am. Chem. Soc. 144:5323-5334 (2022).
Hoang and Lieske, "Effect of Hydrogen Treatments on ZrO2 and Pt/ZrO2 Catalysts," Catalysis Letters 27:33-42 (1994).
Utami et al., "Hydrothermal Preparation of a Platinum-Loaded Sulphated Nanozirconia Catalyst for the Effective Conversion of Waste Low Density Polyethylene into Gasoline-Range Hydrocarbons," RSC Advances 9:41392-41401 (2019).

Wang et al., "Graphene Oxide-Periodic Mesoporous Silica Sandwich Nanocomposites with Vertically Oriented Channels," ACS Nano 4:7437-7450 (2010).
Yang et al., "Graphene-Based Nanosheets with a Sandwich Structure," Angew. Chem. Int. Ed. 49:4795-4799 (2010).
Aaron Sadow, "Strategies for Selective Conversions of Polyolefins in the Institute for Cooperative Upcycling of Plastics (iCOUP)," Fall ACS National Meeting, Aug. 2022.
Yappert et al., "Integrated Multiscale Models for Polymer Upcycling," Poster, Sep. 2021.
U.S. Appl. No. 18/539,495, filed Dec. 14, 2023, first named inventor Aaron D. Sadow.
U.S. Appl. No. 18/662,461, filed May 13, 2024, first named inventor Aaron D. Sadow.
Office Action for U.S. Appl. No. 18/508,055 (Jul. 11, 2024).
Uddhav Kanbur, "Rare-Earth and Zirconium Catalyzed C-H Activation with Applications to Polymer Upcycling," Thesis (Aug. 18, 2022).

* cited by examiner

HDPE                    HDPE-OH

Figure 4

$$CH_4 + AlEt_3 \xrightarrow[\substack{150\ ^\circ C,\ 12\ h \\ -\ Et\text{-}H}]{} Al(CH_3)_x Et_{3-x}$$

Figure 7

SELECTIVE TERMINAL CH ALUMINATION OF SATURATED HYDROCARBONS

This application claims the priority benefit of U.S. Provisional Patent Application Ser. No. 63/277,040 filed Nov. 8, 2021, which is hereby incorporated by reference in its entirety.

GOVERNMENT INTERESTS

This invention was made with government support under DOE Contract No. DE-AC02-07CH11358 and DOE Contract No. DE-AC02-06CH11357, both awarded by U.S. Department of Energy. The government has certain rights in the invention.

FIELD

The present application is directed to a catalyst and its use for the selective functionalization of hydrocarbons.

BACKGROUND

Catalytic methods for the direct introduction of heteroatom functionality into aliphatic hydrocarbons engage oxidations, carbenoid or nitrenoid insertions, or C—H bond dehydrogenative elementation chemistry such as borylation to transform inexpensive chemical feedstocks into value-added products. These methods typically have been developed for activation and transformation of small molecules, such as the oxidation of methane to methanol or the oxidation of cyclohexane to cyclohexanol, or the borylation of aromatic compounds to allow cross-coupling in shortened synthetic routes. These small-molecule C—H bond activations can also be adapted for post-synthesis functionalization of polyolefins to provide functional-group-containing polymers. Such polymers combine the useful physical properties of polyolefins with chemical reactivity needed to improve barrier properties, create adhesive films, or conjugate chains to functional materials to benefit food and biomedical security. This approach, in combination with melt processing, could also allow repurposing of discarded single-use plastics, which are majority contributors to the polymer waste crisis, as new materials with improved biodegradable characteristics.

Recent advances in polyolefin post-synthesis functionalization have relied upon these existing catalytic or radical chemistries, with the processes needing to develop mild conditions to avoid chain cleavage or cross linking from reactions that often accompany C—H bond activations. C—H borylation of polyolefins is catalyzed by molecular rhodium precursors with bis(pinacolato)diboron to provide borylated polyolefins, which are subsequently oxidized to give hydroxy-terminated side chains. Catalytic oxidations, giving hydroxylated polyolefins, and radical functionalization are typically governed by reactant bond strength and rates rebound vs chain scission. Alternatively, functional groups are typically introduced into polystyrene during its synthesis, rely upon heteroatom-containing styrene monomers, rather than post-polymerization conversions. New, organometallic-catalyzed C—H bond activations that avoid single-electron steps leading to chain scission or crosslinking, could also provide the selectivity needed to create value from myriad polyolefin materials.

Aluminum-based reagents are attractive for C—H bond functionalization, particularly in conversions of the massive quantity of currently discarded single-use polyolefins, due to their elemental availability, atom-economical direct syntheses from simple substances (e.g., Al, $H_2$ and alkenes gives alkylaluminums), and wide-ranging and versatile use in synthetic manufacturing. For example, alkylaluminum species can be oxidized with $O_2$ to give alcohols, carboxylated with $CO_2$ to give carboxylic acids, protonated with weak acids to form alkanes, halogenated with electrophilic halogen sources such as $I_2$ to give alkyl halides, used as activators or chain transfer agents in alkene polymerizations, and for carbon-carbon bond formations including carboaluminations or cross-coupling reactions. Unfortunately, hydrocarbon functionalizations utilizing such reagents are surprisingly limited, and catalytic C—H bond aluminations are unknown with commercial alkylaluminum reactants or in conversions of aliphatic C—H bonds. Instead, the only examples involve palladium-catalyzed reactions of diketiminate-supported aluminum(I) or dihydride reagents to give arylaluminum products. New C—H bond alumination reactions employing commercial alkylaluminum reagents for transformations of saturated hydrocarbons could be advantageous for the direct functionalization of polyolefins, as well as other hydrocarbons, to directly provide polar-functional-group-containing compounds.

The present application relates to overcoming deficiencies in the art.

SUMMARY

One aspect of the present application relates to a method of functionalizing a hydrocarbon comprising:

providing a compound of formula (I):

$$Al(R^1)_3 \tag{I}$$

providing a compound of formula (II):

$$Met(R^2)_n@support \tag{II}$$

providing one or more hydrocarbons;

wherein $R^1$ is independently selected at each occurrence thereof from the group consisting of $C_6$-$C_{10}$ aryl and $C_1$-$C_{10}$ alkyl;

Met is a transition metal or lanthanide series metal;

$R^2$ is independently selected at each occurrence thereof from the group consisting of $C_1$-$C_{10}$ alkoxy, $C_6$-$C_{10}$ aryloxy, $(C_6$-$C_{10}$-aryl$)_o$-$C_1$-$C_{10}$-alkoxy, $(C_1$-$C_{10}$-alkyl$)_p$-$C_6$-$C_{10}$-aryloxy, —N($C_1$-$C_{10}$ alkyl)($C_1$-$C_{10}$ alkyl), —C(O)NH($C_1$-$C_{10}$ alkyl), —C(O)N($C_1$-$C_{10}$ alkyl)($C_1$-$C_{10}$ alkyl), —OSi($R^3$)$_3$, and halide;

$R^3$ is independently selected at each occurrence thereof from the group consisting of $C_6$-$C_{10}$ aryl and $C_1$-$C_{10}$ alkyl;

n is 1, 2, 3, or 4;

o is 1, 2, 3, 4, 5, 6, 7, 8, 9, or 10;

p is 1, 2, 3, 4, 5, 6, 7, 8, 9, or 10;

support is selected from the group consisting of silica, alumina, silica/alumina, zeolites, metal oxides, mesoporous oxides, natural clays, and mixtures thereof;

contacting the compound of formula (I) with the compound of formula (II) to form a complex;

contacting the complex with one or more hydrocarbons in a reaction mixture under reaction conditions effective to functionalize the one or more hydrocarbons, wherein $R^1$ is a group that does not produce a hydride under the reaction conditions; and recovering the functionalized one or more hydrocarbons.

Another aspect of the present application relates to a system comprising:

a compound of formula (I):

$$Al(R^1)_3 \qquad (I)$$

a compound of formula (II):

$$Met(R^2)_n@support \qquad (II)$$

wherein $R^1$ is independently selected at each occurrence thereof from the group consisting of $C_6$-$C_{10}$ aryl and $C_1$-$C_{10}$ alkyl;

Met is a transition metal or lanthanide series metal;

$R^2$ is independently selected at each occurrence thereof from the group consisting of $C_1$-$C_{10}$ alkoxy, $C_6$-$C_{10}$ aryloxy, $(C_6$-$C_{10}$-aryl$)_o$-$C_1$-$C_{10}$-alkoxy, $(C_1$-$C_{10}$-alkyl$)_p$-$C_6$-$C_{10}$-aryloxy, —N($C_1$-$C_{10}$ alkyl)($C_1$-$C_{10}$ alkyl), —C(O)NH($C_1$-$C_{10}$ alkyl), —C(O)N($C_1$-$C_{10}$ alkyl)($C_1$-$C_{10}$ alkyl), —OSi($R^3$)$_3$, and halide;

$R^3$ is independently selected at each occurrence thereof from the group consisting of $C_6$-$C_{10}$ aryl and $C_1$-$C_{10}$ alkyl;

n is 1, 2, 3, or 4;

o is 1, 2, 3, 4, 5, 6, 7, 8, 9, or 10;

p is 1, 2, 3, 4, 5, 6, 7, 8, 9, or 10;

support is selected from the group consisting of silica, alumina, silica/alumina, zeolites, metal oxides, mesoporous oxides, natural clays, and mixtures thereof, wherein the compound of formula (I) and the compound of formula (II) are capable of forming a complex which, when contacted with one or more hydrocarbons under reaction conditions, is effective to functionalize the one or more hydrocarbons, with the proviso that $R^1$ is a group that does not produce a hydride under the reaction conditions.

The present application discloses useful methods and systems for functionalizing the terminal carbon of a hydrocarbon via C—H activation. Examples of functionalization include, but are not limited to, introduction of an alcohol, halide, chain extension of the hydrocarbon substrate, as well as cross-coupling of the hydrocarbon substrate. The breadth of the substrate that may be activated and functionalized ranges from, but is not limited to, long chain polymers down to methane. The ability to functionalize methane offers a new route for the synthesis of a myriad of single carbon containing compounds.

BRIEF DESCRIPTION OF THE DRAWINGS

Figure 4:
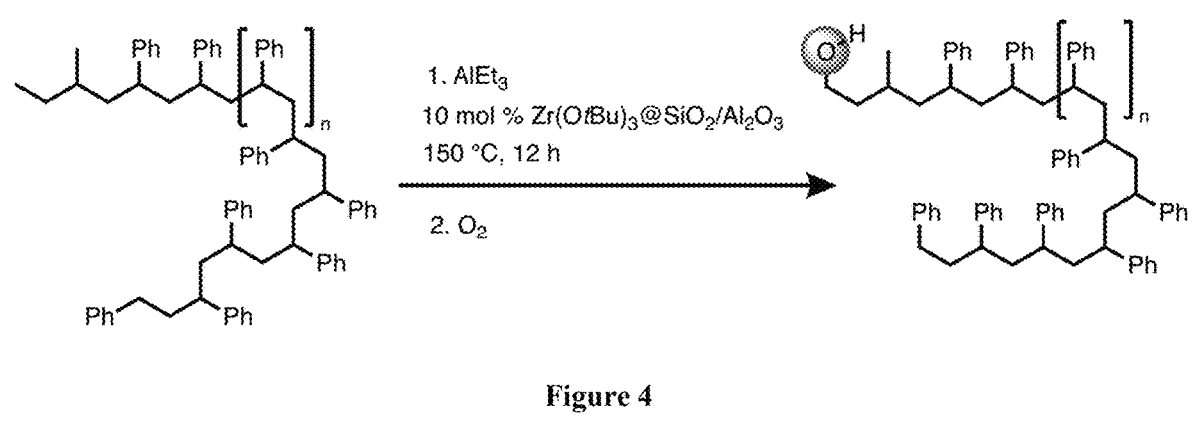

FIG. 4 shows the reaction schematic of the conversion of polystyrene to polystyrene —OH.

FIG. 7 shows the reaction schematic of the alumination of methane.

DETAILED DESCRIPTION

Figure 1:
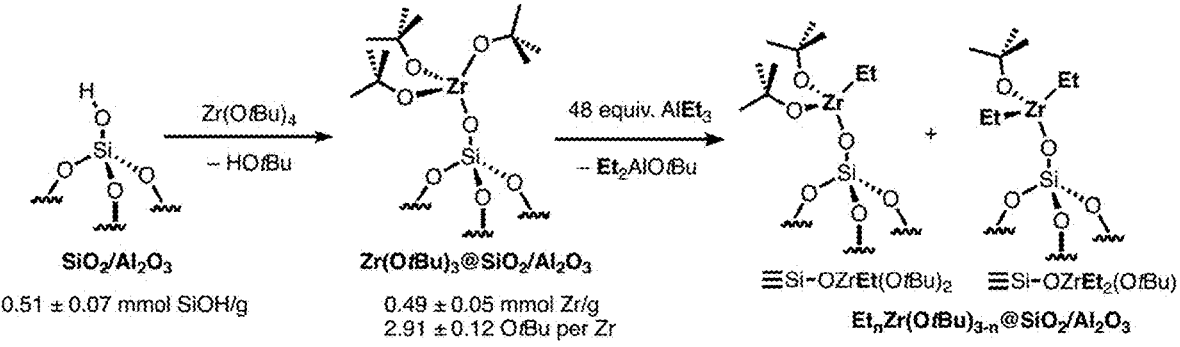
FIG. 1 shows the grafting and ethylation to produce $Et_nZr(OtBu)_{3-n}@SiO_2$—$Al_2O_3$.

One aspect of the present application relates to a method of functionalizing a hydrocarbon comprising:

providing a compound of formula (I):

$$Al(R^1)_3 \qquad (I)$$

providing a compound of formula (II):

$$Met(R^2)_n@support \qquad (II)$$

providing one or more hydrocarbons;

wherein $R^1$ is independently selected at each occurrence thereof from the group consisting of $C_6$-$C_{10}$ aryl and $C_1$-$C_{10}$ alkyl;

Met is a transition metal or lanthanide series metal;

$R^2$ is independently selected at each occurrence thereof from the group consisting of $C_1$-$C_{10}$ alkoxy, $C_6$-$C_{10}$ aryloxy, $(C_6$-$C_{10}$-aryl$)_o$-$C_1$-$C_{10}$-alkoxy, $(C_1$-$C_{10}$-alkyl$)_p$-$C_6$-$C_{10}$-aryloxy, —N($C_1$-$C_{10}$ alkyl)($C_1$-$C_{10}$ alkyl), —C(O)NH($C_1$-$C_{10}$ alkyl), —C(O)N($C_1$-$C_{10}$ alkyl)($C_1$-$C_{10}$ alkyl), —OSi($R^3$)$_3$, and halide;

$R^3$ is independently selected at each occurrence thereof from the group consisting of $C_6$-$C_{10}$ aryl and $C_1$-$C_{10}$ alkyl;

n is 1, 2, 3, or 4;

o is 1, 2, 3, 4, 5, 6, 7, 8, 9, or 10;

p is 1, 2, 3, 4, 5, 6, 7, 8, 9, or 10;

support is selected from the group consisting of silica, alumina, silica/alumina, zeolites, metal oxides, mesoporous oxides, natural clays, and mixtures thereof;

contacting the compound of formula (I) with the compound of formula (II) to form a complex;

contacting the complex with one or more hydrocarbons in a reaction mixture under reaction conditions effective to functionalize the one or more hydrocarbons, wherein $R^1$ is a group that does not produce a hydride under the reaction conditions; and recovering the functionalized one or more hydrocarbons.

Another aspect of the present application relates to a system comprising:

a compound of formula (I):

$$Al(R^1)_3 \qquad (I)$$

a compound of formula (II):

$$Met(R^2)_n@support \qquad (II)$$

wherein $R^1$ is independently selected at each occurrence thereof from the group consisting of $C_6$-$C_{10}$ aryl and $C_1$-$C_{10}$ alkyl;

Met is a transition metal or lanthanide series metal;

$R^2$ is independently selected at each occurrence thereof from the group consisting of $C_1$-$C_{10}$ alkoxy, $C_6$-$C_{10}$ aryloxy, $(C_6$-$C_{10}$-aryl$)_o$-$C_1$-$C_{10}$-alkoxy, $(C_1$-$C_{10}$-alkyl$)_p$-$C_6$-$C_{10}$-aryloxy, —N($C_1$-$C_{10}$ alkyl)($C_1$-$C_{10}$ alkyl), —C(O)NH($C_1$-$C_{10}$ alkyl), —C(O)N($C_1$-$C_{10}$ alkyl)($C_1$-$C_{10}$ alkyl), —OSi($R^3$)$_3$, and halide;

$R^3$ is independently selected at each occurrence thereof from the group consisting of $C_6$-$C_{10}$ aryl and $C_1$-$C_{10}$ alkyl;

n is 1, 2, 3, or 4;

o is 1, 2, 3, 4, 5, 6, 7, 8, 9, or 10;

p is 1, 2, 3, 4, 5, 6, 7, 8, 9, or 10;

support is selected from the group consisting of silica, alumina, silica/alumina, zeolites, metal oxides, mesoporous oxides, natural clays, and mixtures thereof, wherein the compound of formula (I) and the compound of formula (II) are capable of forming a complex which, when contacted with one or more hydrocarbons under reaction conditions, is effective to functionalize the one or more hydrocarbons, with the proviso that $R^1$ is a group that does not produce a hydride under the reaction conditions.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "aryl" means an aromatic monocyclic or multicyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "alkoxy" means groups of from 1 to 10 carbon atoms of a straight, branched, or cyclic configuration and combinations thereof attached to the parent structure through an oxygen. Examples include methoxy, ethoxy, n-propoxy, isopropoxy, n-butoxy, i-butoxy, t-butoxy, phenoxy, cyclopropyloxy, cyclohexyloxy, and the like.

The term "copolymer" refers to a polymer derived from more than one species of monomer.

As used herein, "halide" refers to fluoro, chloro, bromo, or iodo.

The term "hydrocarbon" refers to a compound consisting of hydrogen and carbon. The term is inclusive of both saturated and/or unsaturated aliphatic compounds, aromatic compounds, saturated and/or unsaturated aliphatic compounds substituted with aromatic functional groups, aromatic compounds substituted with saturated and/or unsaturated aliphatic functional groups, and combinations thereof. Aliphatic compounds are inclusive of linear and/or branched and/or cyclic aliphatic compounds.

In some embodiments of the method of functionalizing a hydrocarbon or the system of the present application, $R^1$ is a group that favors alkyl transfer rather than producing a hydride.

In another embodiment of the method of functionalizing a hydrocarbon or the system of the present application, $R^1$ is independently selected at each occurrence thereof from the group consisting of methyl, ethyl, n-propyl, n-butyl, t-butyl, n-pentyl, n-octyl, and phenyl. In some embodiments, $R^1$ is ethyl.

In another embodiment of the method of functionalizing a hydrocarbon or system of the present application, the transition metal or lanthanide series metal is selected from the group consisting of zirconium, titanium, hafnium, vanadium, niobium, tantalum, scandium, yttrium, lanthanum, cerium, praseodymium, neodymium, samarium, europium, gadolinium, terbium, dysprosium, holmium, erbium, thulium, ytterbium, and lutetium. In some embodiments, the transition metal or lanthanide series metal is zirconium.

In another embodiment of the method of functionalizing a hydrocarbon or system of the present application, $R^2$ is independently selected at each occurrence thereof from the group consisting of $C_1$-$C_{10}$ alkoxy, —N($C_1$-$C_{10}$ alkyl)($C_1$-$C_{10}$ alkyl), or halide. In some embodiments, $R^2$ is selected from the group consisting of —OCH$_2$CMe$_3$, —OMe, —OEt, —OnPr, —OiPr, —OnBu, —OCH$_2$CHMe$_2$, —OtBu. —OCH$_2$Ph, —OCHPh$_2$, —OCPh$_3$, —OSiMe$_3$, —OSiEt$_3$, —OSi(OtBu)$_3$, and —OSiPh$_3$. In some embodiments, $R^2$ is —OtBu. In some embodiments, $R^2$ is selected from the group consisting of —NMe$_2$, —NEt$_2$, —NnPr$_2$, and —NiBu$_2$. In some embodiments, $R^2$ is —NMe$_2$.

In another embodiment of the method of functionalizing a hydrocarbon or system of the present application, n is 1. In some embodiments n is 2. In some embodiments n is 3. In some embodiments n is 4.

In another embodiment of the method of functionalizing a hydrocarbon or system of the present application, o is 1. In some embodiments o is 2. In some embodiments o is 3. In some embodiments o is 4. In some embodiments o is 5. In some embodiments o is 6. In some embodiments o is 7. In some embodiments o is 8. In some embodiments o is 9. In some embodiments o is 10.

In another embodiment of the method of functionalizing a hydrocarbon or system of the present application, p is 1. In some embodiments p is 2. In some embodiments p is 3. In some embodiments p is 4. In some embodiments p is 5. In some embodiments p is 6. In some embodiments p is 7. In some embodiments p is 8. In some embodiments p is 9. In some embodiments p is 10.

In another embodiment of the method of functionalizing a hydrocarbon or system of the present application, support is silica. In some embodiments, support is alumina. In some embodiments, support is silica/alumina. In some embodiments, support is zeolites. In some embodiments, support is metal oxides. In some embodiments, support is mesoporous oxides. In some embodiments, support is natural clays.

In some embodiments, the metal oxide is a sulfated metal oxide. For example, the metal oxide can be treated with sulfuric acid. For example, the zirconium oxide can be treated with sulfuric acid for sulfated zirconium oxide (SZO).

In another embodiment of the method of functionalizing a hydrocarbon or system of the present application, the compound of formula (I) is selected from the group consisting of AlMe$_3$, AlEt$_3$, AliBu$_3$, and AlPh$_3$. In some embodiments, the compound of formula (I) is AlEt$_3$.

In another embodiment of the method of functionalizing a hydrocarbon or system of the present application, the compound of formula (II) is selected from the group consisting of Zr(OMe)$_n$@SiO$_2$—Al$_2$O$_3$, Zr(OEt)$_n$@SiO$_2$—Al$_2$O$_3$, Zr(OnPr)$_n$@SiO$_2$—Al$_2$O$_3$, Zr(OiPr)$_n$@SiO$_2$—Al$_2$O$_3$, Zr(OnBu)$_n$@SiO$_2$—Al$_2$O$_3$, Zr(OCH$_2$CHMe$_2$)$_n$@SiO$_2$—Al$_2$O$_3$, Zr(OtBu)$_n$@SiO$_2$—Al$_2$O$_3$, Zr(OCH$_2$CMe$_3$)$_n$@SiO$_2$—Al$_2$O$_3$, and Zr(halide)$_n$@SiO$_2$—Al$_2$O$_3$. In some embodiments, the compound of formula (II) is Zr(OtBu)$_3$@SiO$_2$—Al$_2$O$_3$. In some embodiments, the compound of formula (II) is Zr(OtBu)$_2$@SiO$_2$—Al$_2$O$_3$.

In another embodiment of the method of functionalizing a hydrocarbon of the present application, the material with active sites of formula (II) is treated with R$_3$SiX (R=H or C$_{1-6}$ alkyl, aryl; X=NR'$_2$, Cl, Br, OTF, CH$_2$CH=CH$_2$) to form Met(R$^2$)$_n$@support/SiR$_3$. In some embodiments, Met(R$^2$)$_n$@support/SiR$_3$ is Zr(OR)$_3$@SiO$_2$—Al$_2$O$_3$ and ≡SiO-SiR$_3$. In some embodiments, Met(R$^2$)$_n$@support/SiR$_3$ is Zr(NMe$_2$)$_3$@SiO$_2$—Al$_2$O$_3$ and ≡SiOSiMe$_3$. In some embodiments, Met(R$^2$)$_n$@support/SiR$_3$ is Zr(OtBu)$_3$@SZO and —OSiR$_3$.

In another embodiment of the method of functionalizing a hydrocarbon of the present application, the one or more hydrocarbons is selected from the group consisting of methane, one or more $C_2$-$C_{30}$ hydrocarbons, one or more $C_{31}$-$C_{100}$ hydrocarbons, one or more $C_{101}$-$C_{150}$ hydrocarbons, one or more $C_{150}$-$C_{200}$ hydrocarbons, one or more $C_{201}$ or greater hydrocarbons, one or more $C_{201}$ or greater hydrocarbons, high density polyethylene (HDPE), low density polyethylene (LDPE), polyethylene (PE), polypropylene, high molecular weight isotactic polypropylene (iPP), linear low density polyethylene (LLDPE), polyethylene-polypropylene-copolymers polystyrene (PS), polystyrene 1000 (PS 1000), polyalphaolefin-10, polyalphaolefins, hydrocarbon oils, hydrocarbon waxes, paraffin wax, mineral oils, synthetic oils, and mixtures thereof.

In another embodiment of the method of functionalizing a hydrocarbon of the present application, the one or more $C_2$-$C_{30}$ hydrocarbons is selected from the group consisting of dodecane, eicosane, and mixtures thereof.

In another embodiment of the method of functionalizing a hydrocarbon of the present application, the one or more hydrocarbons is high density polyethylene (HDPE).

In another embodiment of the method of functionalizing a hydrocarbon of the present application, the step of contacting the complex with one or more hydrocarbons under conditions effective to functionalize the one or more hydrocarbons is carried out by adding an electrophile to the reaction mixture to form a functional group on one or more primary carbons of the one or more hydrocarbons.

In another embodiment of the method of functionalizing a hydrocarbon of the present application, the electrophile is selected from the group consisting of $O_2$, $CO_2$, electrophilic halogen, diethyl azodicarboxylate, n-chlorosuccinimide, n-bromosuccinimide, n-iodosuccinimide, ICl, pyridine N-oxide, $H_2O_2$, organic peroxides, and a combination thereof.

In another embodiment of the method of functionalizing a hydrocarbon of the present application, the functional group is selected from the group consisting of alcohol, carboxylic acid, halide, alkyl aluminum, aryl aluminum, and a combination thereof.

In another embodiment of the method of functionalizing a hydrocarbon of the present application, the step of contacting the complex with one or more hydrocarbons under conditions effective to functionalize the one or more hydrocarbons further comprises carrying out catalytic chain growth of the one or more hydrocarbons in the presence of olefins.

In another embodiment of the method of functionalizing a hydrocarbon of the present application, the step of contacting the complex with one or more hydrocarbons under conditions effective to functionalize the one or more hydrocarbons further comprises carrying out an organometal-catalyzed cross-coupling reaction.

In another embodiment of the method of functionalizing a hydrocarbon of the present application, the step of contacting the complex with one or more hydrocarbons under conditions effective to functionalize the one or more hydrocarbons is carried out at temperature of about 50° C. to about 250° C., about 75° C. to about 250° C., about 100° C. to about 250° C., about 125° C. to about 250° C., about 150° C. to about 250° C., about 175° C. to about 250° C., about 200° C. to about 250° C., about 225° C. to about 250° C., about 50° C. to about 225° C., about 50° C. to about 200° C., about 50° C. to about 175° C., about 50° C. to about 150° C., about 50° C. to about 125° C., about 50° C. to about 100° C., about 50° C. to about 75° C., about 75° C. to about 225° C., about 100° C. to about 175° C., about 125° C. to about 175° C., or a or a value within one of these ranges. Specific examples may include about 50° C., about 75° C., about 100° C., about 125° C., about 150° C., about 175° C., about 200° C., about 225° C., about 250° C., or a range between any two of these values In another embodiment of the method of functionalizing a hydrocarbon of the present application, the step of contacting the complex with one or more hydrocarbons under conditions effective to functionalize the one or more hydrocarbons is carried out at temperature of about 150° C.

The above disclosure is general. A more specific description is provided below in the following examples. The examples are described solely for the purpose of illustration and are not intended to limit the scope of the present application. Changes in form and substitution of equivalents are contemplated as circumstances suggest or render expedient. Although specific terms have been employed herein, such terms are intended in a descriptive sense and not for purposes of limitation.

EXAMPLES

General Methods and Techniques

All manipulations were carried out under inert conditions, either using Schlenk techniques or in a glovebox under a purified nitrogen atmosphere, unless stated otherwise. Dry and degassed solvents were used throughout. Pentane and benzene were sparged with nitrogen, passed through activated alumina columns, and stored under nitrogen. Benzene-$d_6$ was degassed via three consecutive freeze-pump-thaw cycles, dried over Na/K alloy, vacuum transferred, and stored over molecular sieves under nitrogen. Triethylaluminum, high density polyethylene (HDPE; $M_n$=7 kDa, $M_w$=26 kDa), a low molecular weight polyethylene (PE) standard ($M_n$=2.1 kDa, $M_w$=2.5 kDa), a moderate molecular weight PE standard ($M_n$=17 kDa, $M_w$=19.8 kDa), low density polyethylene (LDPE; $M_n$=12 kDa, $M_w$=78 kDa), linear low density polyethylene (LLDPE; $M_n$=15.5 kDa, $M_w$=66.3 kDa), isotactic polypropylene (iPP; $M_n$=55 kDa, $M_w$=243 kDa), polystyrene (PS; $M_n$=40.6 kDa, $M_w$=80.4 kDa) and a PS standard ($M_n$=820 Da, $M_w$=900 Da) were purchased from SigmaAldrich and used as received. Polyalphaolefin-10 (PAO-10) was obtained from Chevron Phillips and used as received. Zirconium tetrakis(tert-butoxide) was purchased from Strem Chemicals and used as received. Zirconium ethoxide and zirconium n-propoxide (70% wt. in 1-propanol) were purchased from SigmaAldrich and used as received. Fumed silica (Aerosil) of surface area 300 $m^2$/g was purchased from Evonik, calcined and partially dehydroxylated by heating at 700° C. under dynamic vacuum for 12 h. The accessible OH loading of the surface silanols in partially dehydroxylated Aerosil was 0.46±0.05 mmol/g, measured by titration with $Mg(CH_2Ph)_2(O_2C_4H_8)_2$. Silica-alumina (Grade 135) was purchased from SigmaAldrich, calcined and partially dehydroxylated at 700° C. for 12 h each. Titration of the surface hydroxyl groups in this material with $Mg(CH_2Ph)_2(O_2C_4H_8)_2$ revealed a surface OH loading of 0.51±0.03 mmol/g. γ-alumina (40 $m^2$/g surface area) was purchased from Inframat Advanced Materials, calcined, and partially dehydroxylated at 700° C. for 12 h each. Titration of the surface hydroxyl groups in the γ-alumina with $Mg(CH_2Ph)_2(O_2C_4H_8)_2$ revealed a surface OH loading of xxx±xxx mmol/g.

Fourier transform infrared (FT-IR) spectra and diffuse reflectance infrared Fourier transform (DRIFT) spectra were recorded on a Bruker VERTEX 80 IR spectrometer. Samples for transmission IR were diluted with KBr, finely ground using a mortar and pestle, and pressed into a transparent pellet using a hydraulic press. DRIFT spectra were collected using a Harrick Praying Mantis accessory in a sealed, ambient-pressure sample chamber consisting of a dome with ZnSe windows. Elemental analysis was performed using a Perkin-Elmer 2400 Series II CHN/S at the Iowa State Chemical Instrumentation Facility. Inductively Coupled Plasma-Optical Emission Spectroscopy (ICP-OES) was performed to measure the amount of zirconium present in the catalytic materials. The samples (2.0-4.0 mg each) were digested for 24 h in aqueous HF and aqua-regia (0.18% and 5% respectively) and analyzed in a Perkin Elmer Optima 2100 DV Inductively Coupled Plasma-Optical Emission Spectroscope. Solution-phase $^1H$ NMR and $^{13}C\{^1H\}$ NMR spectra, and 2D $^1H$-$^1H$ COSY and $^1H$-$^{13}C$ HSQC NMR spectra were acquired on a Brucker NEO 400 MHz spectrometer. High temperature solution-phase NMR spectra of polymers were acquired on a Bruker Avance III 600 MHz spectrometer in 1,2-dichlorobenzene-$d_4$.

MALDI-TOF Mass Spectrometry

MALDI-TOF-MS experiments were carried out on a Bruker UltrafleXtreme MALDI-TOF/TOF spectrometer, equipped with a Smartbeam-II™ laser (2 kHz repetition rate). The mass spectra were acquired in both linear positive and reflector positive ion mode. 1000 laser shots were utilized for each measurement. The MALDI-TOF spectra were analyzed, average molecular weights and polydispersities were calculated using the Bruker PolyTools software.

Stock solutions of products were prepared in tetrahydrofuran at a 0.5 mg/mL concentration, and a stock solution of silver nitrate was prepared in a 1:1 (v:v) mixture of tetrahydrofuran and acetonitrile at a concentration of 10 mg/mL. Final sample solutions for spotting were prepared by mixing equal volumes (0.2 mL) of stock solutions of alkanes and silver nitrate. The matrix (2,5-dihydroxybenzoic acid (DHB)) solution was prepared in a 3:2 (v:v) mixture of tetrahydrofuran and methanol at a 10 mg/mL concentration. The dried-droplet method of sample deposition was employed, where 0.5 µL of the sample solution was deposited on the stainless-steel sample plate, followed by 0.5 µL of the matrix solution. The solvents were allowed to evaporate by air-drying.

Example 1 Catalyst Screen

The polyolefin reactant (HDPE: 0.34 g, 0.048 mmol, based on $M_n$=7,000 Da, $M_w$=26,000 Da, Đ=3.8), the supported catalyst ($Zr(OtBu)_3@SiO_2$—$Al_2O_3$: 0.08 g, 0.04 mmol Zr), and triethylaluminum (0.05 g, 0.43 mmol) were loaded into a glass tube equipped with a glass-encapsulated magnetic stirrer. The tube was attached to a closed glass tube with a sidearm containing a re-sealable Teflon-glass valve by a stainless steel UltraTorr o-ring sealed compression fitting. The reaction vessel was heated and stirred in an aluminum block on a stirring-hot plate at 150° C.) to ensure the polymer was above its melting point) for 12 h). The reaction vessel was allowed to cool, and the contents of the tube were quenched by passing dry air into the vessel through the sidearm for 12 h. The crude reaction mixture was washed with $CH_2Cl_2$ (3×5 mL) to remove lower molecular weight species; the washings were combined, solvent was evaporated, and the residue was quantified and analyzed by NMR spectroscopy and GC-MS. The conditions described here typically did not provide significant quantities of alkanes or alcohols over the $C_6$-$C_{40}$ range measured by these methods. The remaining functionalized polyolefin was dissolved in 1,2-dichlorobenzene at 120° C. and filtered at that temperature to remove the catalyst. Upon cooling, the polymer precipitates. Additional $CH_2Cl_2$ was added to facilitate precipitation. The supernatant liquid was decanted, and the solid polymer was washed with $CH_2Cl_2$ (3×5 mL), dried in vacuo, quantified on an analytical balance, and analyzed by IR and NMR spectroscopy.

During the study of high density polyethylene (HDPE) alumination, negligible amounts of low molecular products were isolated from the reaction of HDPE ($M_n$=6.2 kDa, $M_w$=38.6 kDa, Đ=6.2), $AlEt_3$, and catalytic quantities of $Zr(OCH_2CMe_3)_2@SiO_2$—$Al_2O_3$ (obtained from the reaction of $Zr(CH_2CMe_3)_2@SiO_2$—$Al_2O_3$ and $O_2$) at 150° C. for 12 hours. The recovered polymer, obtained in high yield after quenching the reaction mixture with dry air, contained hydroxy groups as indicated by a broad IR signal at 3436 $cm^{-1}$. Importantly, the almost identical molecular weight and chain-length distribution as the starting HDPE (Table 1) indicate that β-alkyl elimination steps leading to chain cleavages are insignificant. Slow β-alkyl elimination relative to chain transfer, or higher selectivity for chain end metalation, provide possible rationalization for the observed chemistry. Both effects would be favored by steric hinderance at the zirconium center, involving retention of one $OCH_2CMe_3$ as an ancillary ligand and Zr—$CH_2CH_3$ as the reacting moiety, rather than the less hindered ZrH intermediate proposed in chain cleavage chemistry.

TABLE 1

| | | | | | Yield |
|---|---|---|---|---|---|
| # | Catalyst | $M_{n\,post}$ | $M_{w\,post}$ | Đ $_{post}$ | (%) |
| 1 | $Zr(OCH_2CMe_3)_2@SiO_2$—$Al_2O_3$ | 6200 | 39000 | 6.3 | 24 |
| 2 | $Zr(OtBu)_3@SiO_2$—$Al_2O_3$ | 8000 | 26400 | 3.3 | 78 |
| 3 | $Zr(OtBu)_3@SiO_2$ | 9600 | 32200 | 3.3 | 17 |
| 4 | $Zr(OtBu)_3@\gamma$—$Al_2O_3$ | 10500 | 33000 | 3.1 | 82 |
| 5 | $Zr(OEt)_n@SiO_2$—$Al_2O_3$ | 10100 | 31800 | 3.1 | 71 |
| 6 | $Zr(OnPr)_n@SiO_2$—$Al_2O_3$ | 13400 | 34600 | 2.6 | 11 |

Starting HDPE: $M_n$ = 7000 Da, $M_w$ = 26000 Da, Đ = 3.8
Yield = (mol PE-OH/mol $PE_{init}$)*100

Based on the results presented in Table 1, bulky zirconium tert-butoxide supported on silica alumina $Zr(OtBu)_3@SiO_2$—$Al_2O_3$ was targeted as the catalyst, in combination with $AlEt_3$ as the reagent for CH alumination. Silica-alumina, heated at 700° C. under vacuum ($SiO_2$—$Al_2O_3$; 0.51 mmol SiOH/g), was reacted with $Zr(OtBu)_4$ to give $Zr(OtBu)_3@SiO_2$—$Al_2O_3$(FIG. 1).

Figure 2:
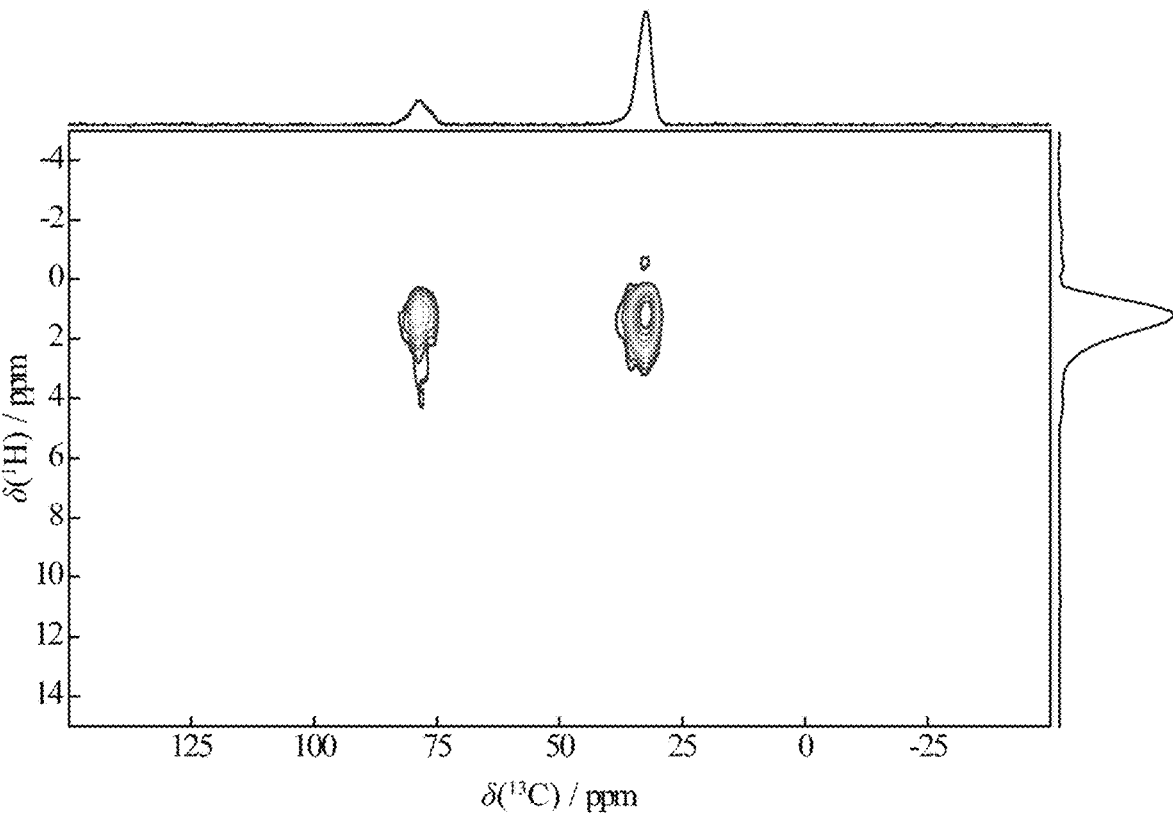
FIG. 2 shows the correlations in $CMe_3$ groups of $Zr(OtBu)_3@SiO_2$—$Al_2O_3$ in a $^{13}C\{^1H\}$ HETCOR spectrum.
Figure 3:
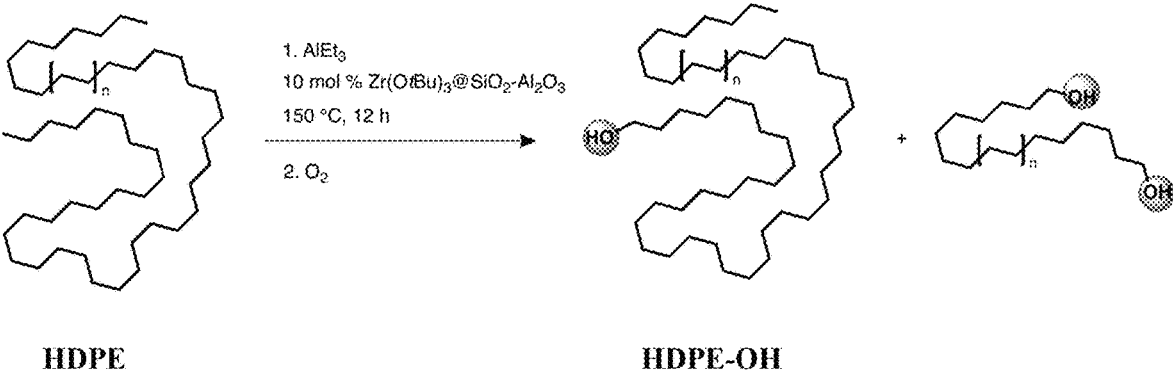
FIG. 3 shows the reaction schematic of the conversion of high density polyethylene (HDPE) to HDPE-OH.

The band at 3740 $cm^{-1}$ in the diffuse reflectance infrared Fourier transform spectrum (DRIFTS) of $SiO_2$—$Al_2O_3$, assigned to the $\nu_{SiOH}$ of isolated silanols, was not detected in $Zr(OtBu)_3@SiO_2$—$Al_2O_3$, suggesting near-quantitative consumption of isolated Si—OH groups. The Zr loading, determined by inductively coupled plasma-optical emission spectroscopy (ICP-OES) measurements, was 4.43 wt % (0.49 mmol Zr/g). Comparison of this value and the SiOH in $SiO_2$—$Al_2O_3$ corroborates the near-quantitative grafting process. Titration, in combination with the Zr loading, revealed 2.91±0.12 OtBu groups per zirconium center. A dynamic nuclear polarization (DNP)-enhanced cross polarization magic angle spinning (CP-MAS) $^{13}C$ nuclear magnetic resonance (NMR) spectrum contained signals at 80 ppm and 33 ppm, assigned to the quaternary carbon and methyl groups, respectively, of the OtBu. The two signals correlate with the $^1H$ methyl signal at 1.3 ppm in a $^{13}C\{^1H\}$ heteronuclear correlation (HETCOR) experiment (FIG. 2).

These data are consistent with $\equiv$SiO—Zr(OtBu)$_3$ groups almost exclusively as the surface species in the sample.

Figure 5:
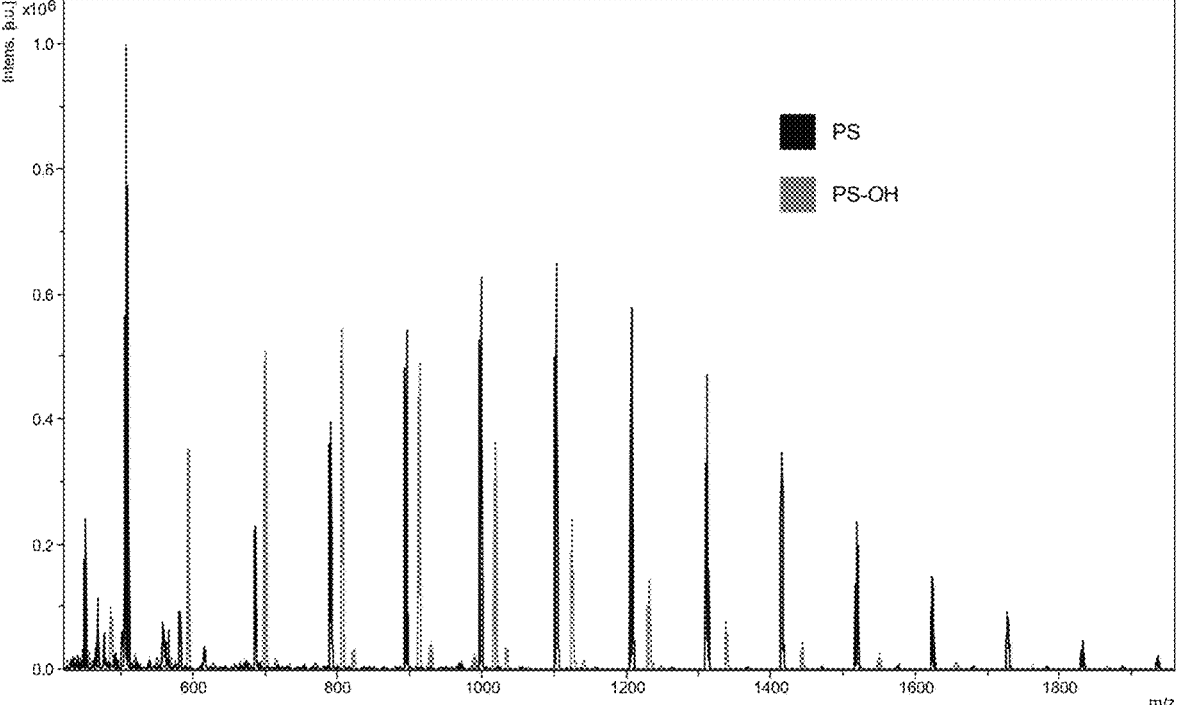
FIG. 5 shows the overlaid MALDI-TOF-MS spectra of polystyrene (PS 1000, dark gray, $M_n$=980, Đ=1.09) starting material and functionalized polystyrene (PS-OH, light gray, $M_n$=760, Đ=1.09) products.

AlEt$_3$ transfers ethyl groups to Zr(OtBu)$_3$@SiO$_2$—Al$_2$O$_3$, giving Et$_n$Zr(OtBu)$_{3-n}$@SiO$_2$—Al$_2$O$_3$ as the site mediating C—H bond metalation; this species contrasts with ZrH@SiO$_2$—Al$_2$O$_3$ observed in the PE hydrogenolysis or C—C alumination with AliBu$_3$ or AlH$_3$ as hydride transfer agents. Zr(OtBu)$_3$@SiO$_2$—Al$_2$O$_3$ (0.009 mmol Zr) and excess AlEt$_3$ react at room temperature in benzene-d$_6$ to provide AlEt$_x$(OtBu)$_{3-x}$. $^1$H NMR signals at 0.15 ppm and 1.30 ppm, attributed to AlCH$_2$CH$_3$ and AlCH$_2$CH$_3$, respectively, are distinct from the resonances of residual AlEt$_3$. A singlet at 1.19 ppm was assigned to the t-butoxy group of AlEt$_x$(OtBu)$_{3-x}$ species on the basis of a multiplicity-edited $^1$H-$^{13}$C HSQC. Quantification by NMR integration vs an internal standard revealed 0.0127 mmol OtBu transferred to Al, corresponding to 47% of the total t-butoxy groups, leaving approximately 53% attached to Zr. A ~1:1 mixture of $\equiv$SiO—ZrEt(OtBu)$_2$ and $\equiv$SiO—ZrEt$_2$OtBu (FIG. 5) is consistent with this data, as well as 1:1 $\equiv$SiO—ZrEt$_3$ and $\equiv$SiO—Zr(OtBu)$_3$, and combinations therein are indistinguishable using these analytical methods. A small amount of ethane was also observed at 0.80 ppm, formed most likely from the reaction of free AlEt$_3$ with uncapped surface OH groups (~0.02 mmol/g).

Advantaged by its convenient synthesis, Zr(OtBu)$_3$@SiO$_2$—Al$_2$O$_3$ is also superior to Zr(OCH$_2$CMe$_3$)$_2$@SiO$_2$—Al$_2$O$_3$ for CH alumination of HDPE. HDPE (0.34 g, 0.048 mmol chains estimated from M$_n$, M$_n$=7,000 Da, M$_w$=26,000 Da, Đ=3.8) and AlEt$_3$ (0.43 mmol) react in the presence of Zr(OtBu)$_3$@SiO$_2$—Al$_2$O$_3$ (0.04 mol Zr) at 150° C. for 12 hours under solvent-free conditions, quenched with dry air, and extracted with 1,2-dichlorobenzene to afford a polymeric residue HDPE-OH.

Example 2 Functionalization of Various Polymers by Zr(OtBu)$_3$@SiO$_2$—Al$_2$O$_3$ Following a similar procedure to that described in Example 1, several polymers were successfully functionalized by Zr(OtBu)$_3$@SiO$_2$—Al$_2$O$_3$.

A $^1$H NMR spectrum of HDPE-OH dissolved in 1,2-dichlorobenzene-d$_4$ at 120° C. revealed a signal at 3.6 ppm, which correlated in a $^1$H-$^{13}$C multiplicity-edited HSQC experiment with a $^{13}$C NMR signal at 68 ppm, indicative of a —CH$_2$—OH unit. Integration of CH$_2$OH versus the Si(SiMe$_3$)$_4$ internal standard provides the yield of alcohol functionality in moles, divided by the initial amount of polymer (in moles) gives the percent yield of functionalized chains (see Table 2). Analysis of the product by gel permeation chromatography (GPC) shows a negligible change in the molecular weight distribution post-reaction (M$_n$=8,000 Da, Đ=3.3).

TABLE 2

CH Alumination of polyolefins catalyzed by
Zr(OtBu)$_3$@SiO$_2$—Al$_2$O$_3$

| # | Polymer | M$_{n\ init}$ (Da) | M$_{w\ init}$ (Da) | Đ$_{init}$ | M$_{n\ post}$ (Da) | M$_{w\ post}$ (Da) | Đ$_{post}$ | Yield (%) |
|---|---------|---------|---------|------|---------|---------|------|------|
| 1 | HDPE | 7000 | 26000 | 3.8 | 8000 | 26400 | 3.3 | 78 |
| 2 | PE | 2100 | 2500 | 1.2 | 2100 | 2600 | 1.2 | 86 |
| 3 | PE | 17000 | 19800 | 1.1 | 17500 | 19200 | 1.1 | 71 |
| 4 | LDPE | 12000 | 78000 | 6.5 | 10000 | 84000 | 8.4 | 125 |
| 5 | LLDPE | 15500 | 66300 | 4.3 | 18500 | 64500 | 3.5 | 153 |
| 6 | iPP | 55000 | 243000 | 4.4 | 37000 | 128000 | 3.4 | |

TABLE 2-continued

CH Alumination of polyolefins catalyzed by
Zr(OtBu)$_3$@SiO$_2$—Al$_2$O$_3$

| # | Polymer | M$_{n\ init}$ (Da) | M$_{w\ init}$ (Da) | Đ$_{init}$ | M$_{n\ post}$ (Da) | M$_{w\ post}$ (Da) | Đ$_{post}$ | Yield (%) |
|---|---------|---------|---------|------|---------|---------|------|------|
| 7 | PS 1000 | 820 | 900 | 1.1 | 840 | 940 | 1.1 | 109 |
| 8 | PS | 40600 | 80400 | 2.0 | 46100 | 97600 | 2.1 | — |

Yield = (mol CH$_2$—OH/mol polymer$_{init}$) * 100

Discussion

Silica and silica-alumina supports affect the performance of alkylzirconium and alkoxyzirconium in deconstruction of polyolefins via C—C alumination, and small changes in pre-catalyst affect C—H vs C—C alumination. A few related catalytic materials, with silica or γ-alumina as support materials or zirconium sites with smaller alkoxy groups, were investigated for comparison (Table 1). Zr(OtBu)$_3$@SiO$_2$, AlEt$_3$, and HDPE react to afford HDPE-OH in a low yield (17%). During this reaction, the catalytic material becomes an intense brown color, SS $^{27}$Al NMR spectroscopy indicates that new aluminum sites are inserted into the support, and soluble ethylsilane species are formed, indicating that alumination and degradation of the support has occurred. Zr(OtBu)$_3$@γ-Al$_2$O$_3$ catalyzes alumination to provide HDPE-OH in a good yield (82%). This reaction leads to catalyst decomposition. EtSi formation is decreased, and catalyst turnovers increase when Zr(OtBu)3@SiO$_2$—Al$_2$O$_3$ is treated with Me$_3$SiC$_3$H$_5$ to cap additional SiOH, AlOH, or BAS on the surface Effects of the alkoxide ligands were also investigated. Zr(OEt)$_3$@SiO$_2$—Al$_2$O$_3$ catalyzed alumination of HDPE to afford HDPE-OH in a 71% yield. Zr(OnPr)$_n$(nPrOH)$_q$@SiO$_2$—Al$_2$O$_3$, however, was relatively inactive toward the conversion of HDPE to HDPE-OH (11% yield) with AlEt$_3$, likely due to coordinating 1-propanol species in the inner coordination sphere of zirconium, inhibiting the ethylation of zirconium centers with triethylaluminum.

On the basis of these results, Zr(OtBu)$_3$@SiO$_2$—Al$_2$O$_3$ was further studied as the most convenient and most active catalyst for CH alumination of polyolefins and other hydrocarbons. Two monodisperse PE samples (M$_n$=2,100 Da, Đ=1.2; M$_n$=17,000 Da, Đ=1.1) were hydroxylated in good yields (71% and 86%, respectively), giving products with similar molecular weight as the starting resin (Table 2). Highly branched LDPE (M$_n$=12,000 Da, Đ=6.5) and LLDPE (M$_n$=15,000 Da, Đ=4.3) provides LDPE-OH and LLDPE-OH in 125% and 153% yields, respectively, corresponding to more than one hydroxy group per chain. High molecular weight isotactic polypropylene iPP-OH is also produced by the zirconium-catalyzed alumination. Although the decrease in M$_n$ of the iPP sample is indicative of unwanted C—C bond cleavage, fewer than one cut per original chain is suggested by the reduction in molecular weight by only ca. 35% and the lack of small oligomeric fatty alcohols detected in the quenched reaction mixture.

Reactions of the branched chains of high grade synthetic lubricant polyalphaolefin-10 (0.10 mmol, M$_n$=640 Da, Đ=1.0) with AlEt$_3$ (2.00 mmol) was also catalyzed by Zr(OCH$_2$CMe$_3$)$_3$@SiO$_2$—Al$_2$O$_3$ (0.02 mmol Zr) at 150° C. for 12 h, providing an oil with 68% of chains containing alcohol functionality. NMR and IR spectroscopy, and matrix-assisted laser desorption ionization-time of flight-mass spectrometry (MALDI-TOF-MS) data showed similar features as the functionalized polymers above. The $^1$H NMR signals between 3-4.5 ppm correlate with $^{13}$C signals between 53-70 ppm in a phase-sensitive $^1$H-$^{13}$C HSQC experiment, consistent with —CH$_2$—OH and —CH—OH groups. The MALDI-TOF spectrum revealed the presence of species of the type [C$_n$H$_{2n+2}$Ag]$^+$ and [C$_n$H$_{2n+2}$OAg]$^+$ that correspond to silver adducts of alkanes and monoalcohols.

Solution phase investigations of CH alumination of polystyrene (PS) were motivated by its low barrier toward chain scission, which leads to degradation under melt-phase conditions, and its appreciable solubility at room temperature. Reaction of polystyrene (0.11 mmol PS 1000; M$_n$=980 Da, Đ=1.09, from MALDI analysis) with AlEt$_3$ (12.5 equiv. with respect to PS chains) is catalyzed by Zr(OtBu)$_3$@SiO$_2$—Al$_2$O$_3$ (0.03 mmol Zr) at 120° C. in toluene for 12 h; subsequent oxidation with dry air provided PS-OH (M$_n$=760 Da, Đ=1.09, from MALDI analysis).

A broad $^1$H NMR signal at 3.7-4.2 ppm was assigned to CH$_2$OH end groups based on correlation with a $^{13}$C NMR signal at 60 ppm and phase in a phase-sensitive $^1$H-$^{13}$C HSQC experiment. The MALDI-TOF-MS of the hydroxylated polystyrene (FIG. 5) contained a distribution of peaks separated by 104 Da, corresponding to the mass of the styrene monomer, and increased by 16 m/z compared to the peaks of the low dispersity PS 1000. PS 1000 was not detected in the hydroxylated sample, while the former pattern and a second distribution of lower intensity peaks increased by 32 Da compared to PS 1000 peaks were assigned to an approximately 11:1 ratio of monohydroxylated and dihydroxylated PS-OH. High molecular weight polystyrene (0.025 mmol chains; M$_n$=40,600 Da, Đ=2.0) and AlEt$_3$ also react in the presence of Zr(OtBu)$_3$@SiO$_2$—Al$_2$O$_3$ in toluene over 12 h at 120° C. to give a material with equivalent M$_n$ and Đ to the starting polystyrene, now terminated in hydroxy groups as evidenced by a $^1$H-$^{13}$C phase sensitive HSQC, IR, and MALDI-TOF-MS experiments. Thus, the reactivity of C—H bonds for Zr-catalyzed alumination in PS shows the high propensity for methyl end-group activation.

The products of polymer CH alumination predominantly contain terminal hydroxy groups (CH$_2$OH), which could form via selective zirconation of methyl groups followed by transfer of the polymeryl chain to aluminum. Conversions of atomically precise linear and cyclic small molecules were investigated to probe the relevant and accessible elementary steps in this CH alumination to assess relative rates of β-alkyl elimination compared to metalation and chain transfer and selectivity for C—H bond activation between methyl, methylene, and methine groups, as well as further demonstrate the utility of this hydrocarbon functionalization.

Based on the apparently methyl-selective CH alumination of polymers, methyl-group-free cycloalkanes could either be inert to alumination, give cycloalkanols (after workup) if β-alkyl elimination is slower than chain transfer to aluminum, or give linear products if ring-opening β-alkyl elimination is fast compared to those steps. Reaction of cyclooctane (3.06 mmol) and AlEt$_3$ (3.00 mmol) catalyzed by Zr(OtBu)$_3$@SiO$_2$—Al$_2$O$_3$ (0.05 mmol Zr) at 150° C. for 12 h, followed by quenching with dry air, results in 86% conversion to linear alcohols. Remarkably, 1-hexadecanol was the major product (66%) formed along with some of its isomers and higher oligomers up to C$_{44}$, while cyclooctanol, 1-octanol, 1,8-octanediol, and oct-7-en-1-ol were not detected in the reaction mixture. Likely, metalation of cyclooctane gives cyclooctylzirconium, followed by rapid β-alkyl elimination affords ring-opened Zr—(CH$_2$)

$_6$CH=CH$_2$ intermediate. Metalation of another cyclooctane then generates 1-octene. Dimerization or oligomerization of 1-octene, followed by chain transfer to aluminum provide the observed C$_{8n}$-sized products (n>1). The formation of even chain lengths, not equal to multiples of eight, likely results from Zr-catalyzed ethylalumination of the alkenes generated by β-alkyl elimination. These results, surprisingly, indicate that zirconation of secondary C—H bonds readily occurs and that β-alkyl elimination is fast compared to the exchange of chains between zirconium and aluminum. In addition, cyclooctane metalation by an oct-7-enylzirconium is also faster than chain transfer to aluminum and perhaps less surprising, unsaturation leads to chain growth.

Alternatively, conversions of atomically precise linear hydrocarbons, resulting in longer or shorter chain lengths of odd or even length, could also identify CH$_2$ metalation and/or β-alkyl elimination steps. The reaction of eicosane (C$_{20}$H$_{42}$, 1.10 mmol) with AlEt$_3$ (0.59 mmol) in the presence of Zr(OtBu)$_3$@SiO$_2$—Al$_2$O$_3$ (0.02 mmol Zr) at 150° C. for 12 h followed by oxidation with dry air provides a ~6:1 molar mixture of eicosane:1-eicosanol (0.16 mmol, 27%), as quantified by GC-MS. Similarly, reaction of n-dodecane (0.88 mmol) and AlEt$_3$ (0.60 mmol) in the presence of Zr(OtBu)$_3$@SiO$_2$—Al$_2$O$_3$ (0.02 mmol) provides 1-dodecanol (0.24 mmol, 40%) after workup. Shorter or longer alkyl chains were not detected, although some 1,12-dodecane diol was formed.

Yields and conversion of hydrocarbons are improved using Zr(OtBu)$_3$@SiO$_2$—Al$_2$O$_3$ treated with Me$_3$SiC$_3$H$_5$ (Table 3). The side reaction of AlEt$_3$ and the surface of SiO$_2$ or SiO$_2$—Al$_2$O$_3$, which leads to catalyst deactivation and formation of soluble ethylsilane species, is inhibited by surface silylation with Me$_3$SiC$_3$H$_5$ resulting in no formation of ethylsilane. As a result, the concentration (and molar ratio) of AlEt$_3$ in the reaction can be increased using Zr(OtBu)$_3$@SiMe$_3$/SiO$_2$—Al$_2$O$_3$ leading to a decrease in catalyst degradation. Following the generation of the active Zr(OtBu)$_3$ site, the material is treated with Me$_3$SiC$_3$H$_5$ to passivate any remaining ≡Si—OH that may are prone to deactivation by AlEt$_3$.

TABLE 3

| # | Substrate | Oxide$^a$ | Yield$^b$ (%) |
|---|---|---|---|
| 1 | n-C$_{12}$H$_{26}$ | SiO$_2$—Al$_2$O$_3$ | 27% |
| 2 | n-C$_{12}$H$_{26}$ | Me$_3$Si—SiO$_2$—Al$_2$O$_3$ | 31% |
| 3 | n-C$_{12}$H$_{26}$ | SZO$_{300}$ | 21% |
| 4 | n-C$_{12}$H$_{26}$ | Me$_3$Si—SZO | 25% |
| 5 | n-C$_{12}$H$_{26}$ | ≡Si—OH . . . Al(OR$^F$)$_3$ | 7% |
| 6 | n-C$_{12}$H$_{26}$ | ZrO$_2$ | 20% |

Conditions: nC$_{12}$H$_{26}$ (0.88 mmol), AlEt$_3$ (0.61 mmol), Zr (0.019 mmol), 150° C., 12 hours, quenched with dry air at 0° C. for 12 hours.
$^a$prepared by contacting oxides with Zr(O$^t$Bu)$_3$
$^b$NMR yield.

These comparisons of cyclooctane and dodecane, as well as iPP and PS, first indicate that although C—H bond activation of methylene groups is fast in cyclooctane, reactions of methyl groups are considerably faster than cleavage of secondary, tertiary, and aromatic C—H bonds. Remarkably, this zirconium/aluminum system is also not effective for C-D bond activation. Catalytic experiments involving dodecane-d$_{26}$ returned hydrocarbon starting material, and dodecanol-d$_{25}$ was not detected by $^1$H and $^2$H NMR spectroscopy or GC-MS. In fact, the region between 3-4 ppm in the $^2$H NMR spectrum was notably free of signals typically characteristic of HO—CD$_2$-R. In addition, reactions involving 1:1 mixtures of dodecane and dodecane-d$_{26}$ (0.55 mmol each) afforded 1-dodecanol (0.2 mmol), while dodecanol-$d_{25}$ was not detected. These observations indicate that the CH activation is governed by a very large isotope effect, greater than the typical kinetic isotope effect (KIE) of 5-6 typically associated with σ-bond metathesis-type hydrocarbon metalations using homogeneous d[0] organometallics. The surface organometallic catalysts may also involve adsorption of hydrocarbons on the surface and at the zirconium site, leading to an equilibrium isotope effect (EIE) favoring coordination of C—H bonds of dodecane and $AlEt_3$ over C-D in dodecane. Combination of large EIE and KIE could disfavor metalation of dodecane-$d_{26}$. A related combination of equilibrium binding and primary CH bond activation may also lead to selective end-group activation.

Figure 6:
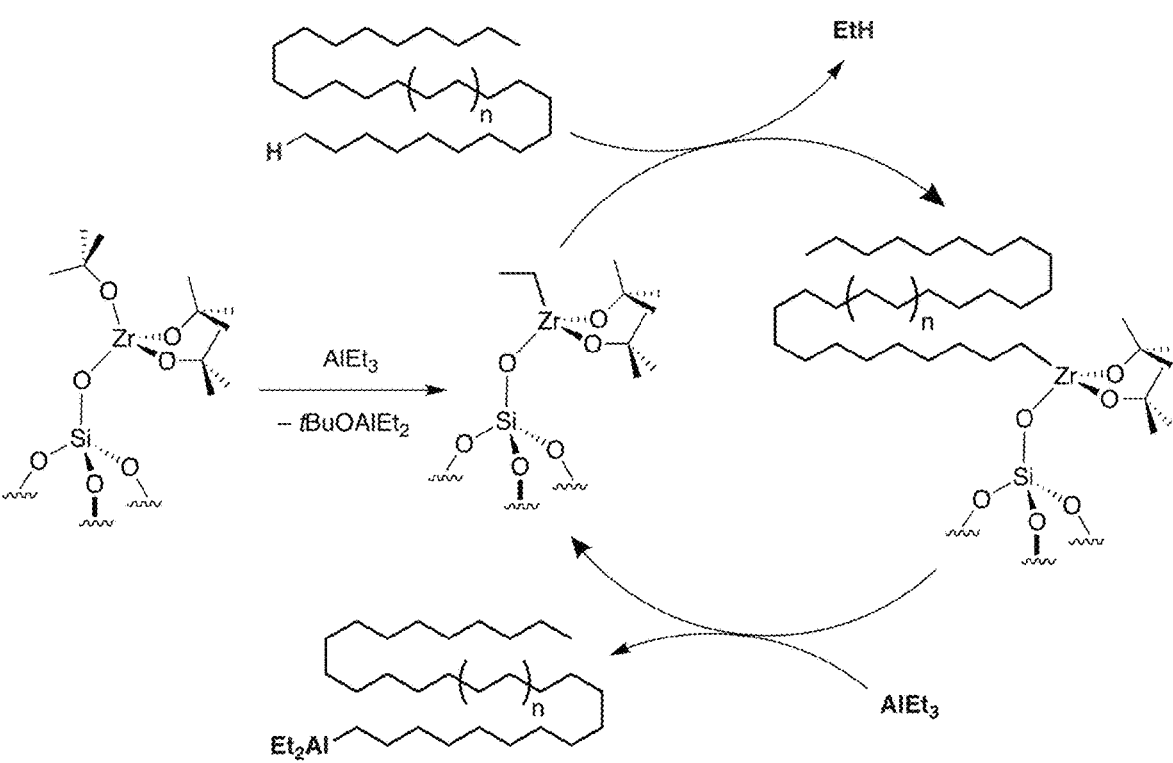
FIG. 6 shows the proposed catalytic cycle for terminal CH alumination of aliphatic hydrocarbons.

The comparisons also reveal that relative rates of these elementary steps are affected by substitution with β-alkyl elimination>chain transfer for secondary alkyls [Zr]CH(CH$_2$R)$_2$, chain transfer>β-alkyl elimination for primary [Zr]CH$_2$CH$_2$R, and chain transfer ~β-alkyl elimination for primary branched alkyls [Zr]CH$_2$(CHR$_2$)$_2$ in this Zr(OtBu)$_3$@SiO$_2$—Al$_2$O$_3$/AlEt$_3$ system. In combination, these factors give high selectivity for chain end functionalization rather than deconstruction. A simple, two-step catalytic cycle may be postulated (FIG. 6), involving metalation of the methyl end group of the polymer chain by surface supported zirconium ethyl species to generate a new zirconium polymeryl species and ethane elimination. Chain transfer of the polymeryl species from zirconium to aluminum, regenerating Zr-Et groups and polymeryl-AlEt$_2$ species.

Figure 7:
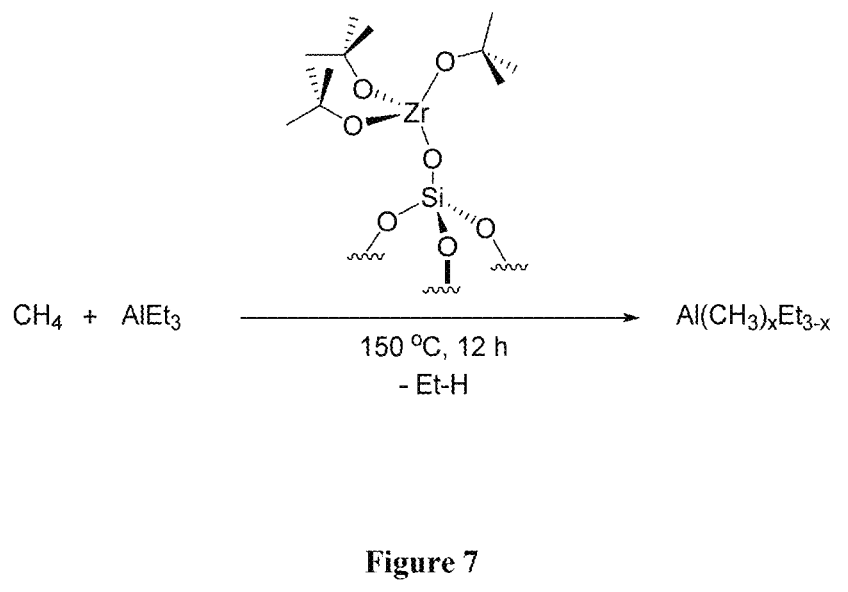

Given the apparently facile metalation of the least hindered C—H bonds in polyolefins, polyalphaolefin lubricants, and even liquid hydrocarbons, the smallest hydrocarbon methane was investigated as a substrate for CH alumination. While $AlEt_3$ is readily synthesized from Al, $C_2H_4$ and $H_2$, $AlMe_3$ involves a multistep process. Thus, direct synthesis of AlMe species from methane and triethylaluminum could be considerably more efficient. Supported alkoxyzirconium catalysts, $AlEt_3$, and $CH_4$ were heated at 150° C. for 12 hours (FIG. 7), and then analyzed by $^1H$ NMR spectroscopy. The broad $^1H$ NMR singlet at –0.07 ppm in the spectrum of the reaction catalyzed by Zr(OtBu)$_3$@SiO$_2$—Al$_2$O$_3$, for example, was readily assigned as an AlMe group (23% yield, 21 TON) through a $^1H$-$^{13}C$ multiplicity edited HSQC experiment. Zr(OtBu)$_3$@SiO$_2$—Al$_2$O$_3$ was the most effective of a few related zirconium catalysts (Table 4).

TABLE 4

| # | Catalyst | Yield[a] (%) | TON[b] |
|---|---|---|---|
| 1 | Zr(OtBu)$_3$@SiO$_2$—Al$_2$O$_3$ | 23 | 21 |
| 2 | Zr(OtBu)$_3$@SiO$_2$ | 4 | 3 |
| 3 | Zr(OtBu)$_3$@γ—Al$_2$O$_3$ | 18 | 14 |
| 4 | Zr(OMe)$_n$@SiO$_2$—Al$_2$O$_3$ | 15 | 11 |
| 5 | Zr(OEt)$_n$@SiO$_2$—Al$_2$O$_3$ | 14 | 11 |
| 6 | Zr(OnPr)$_n$@SiO$_2$—Al$_2$O$_3$ | 3 | 3 |

Conditions: CH$_4$ (700 psi, 2.04 mmol), AlEt$_3$ (0.60 mmol), Zr (0.008 mmol), 150° C., 12 hours.
[a]NMR yield obtained by integration of methyl aluminum signals (CH$_3$Al) against an internal standard (hexamethylbenzene), with respect to AlEt$_3$.
[b]TON = mol CH$_3$Al/mol Zr This new catalytic C—H bond functionalization reaction is effective on hydrocarbon chains, ranging in size from macromolecules representing the largest all the way to the smallest molecule of methane. The formation of alkylaluminum species as the primary products allows for versatile subsequent transformations, such as the oxygenation with O$_2$ employed here, as well as carboxylation with CO$_2$ or halogenation with electrophilic halogen sources, catalytic chain growth in the presence of olefins, or organometal-catalyzed cross-coupling.

A two-step catalytic sequence is proposed, involving hydrocarbon zirconation followed by heterobimetallic metathetical alkyl exchange of surface zirconium hydrocarbyl species and ethylaluminum. Production of terminal alcohols from linear and branched polyolefins with only minor changes in molecular weight indicates that this catalytic method is remarkably selective toward activation of the C—H bonds in methyl groups. The earth abundant, inexpensive, and readily available alkoxylzirconium molecular catalyst precursor and triethylaluminum reagent further add to the benefits of this new transformation, which is nonetheless complementary to our recently reported catalytic C—C alumination reaction. In that process, involving catalytic hydridozirconium sites, β-alkyl elimination was competitive with or faster than chain transfer to aluminum. Both processes offer a direct and sustainable route to fatty alcohols and fatty acids, which are generally biodegradable, as an environmentally friendly end of life for used polyolefins.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A method of functionalizing a hydrocarbon comprising: providing a compound of formula (I):

Al(R$^1$)$_3$     (I);

providing a compound of formula (II):

Met(R$^2$)$_n$@support     (II);

providing one or more hydrocarbons; wherein
R$^1$ is independently selected at each occurrence thereof from the group consisting of C$_6$-C$_{10}$ aryl and C$_1$-C$_{10}$ alkyl;
Met is selected from the group consisting of zirconium, titanium, hafnium, scandium, yttrium, lanthanum, and lutetium;
R$^2$ is C$_1$-C$_4$ alkoxy;
n is 1, 2, 3, or 4; and
support is alumina or silica/alumina;
contacting the compound of formula (I) with the compound of formula (II) to form a complex;
contacting the complex with one or more hydrocarbons in a reaction mixture under reaction conditions effective to functionalize the one or more hydrocarbons, wherein R$^1$ is a group that does not produce a hydride under the reaction conditions; and recovering the functionalized one or more hydrocarbons.

2. The method of claim 1, wherein R$^1$ is independently selected at each occurrence thereof from the group consisting of methyl, ethyl, n-propyl, n-butyl, t-butyl, n-pentyl, n-octyl, and phenyl.

3. The method of claim 2, wherein R$^1$ is ethyl.
4. The method of claim 1, wherein Met is zirconium.
5. The method of claim 1, wherein R$^2$ is —OtBu.
6. The method of claim 1, wherein n is 3.
7. The method of claim 1, wherein the support is silica/alumina.

8. The method of claim 1, wherein the compound of formula (I) is selected from the group consisting of $AlMe_3$, $AlEt_3$, $AliBu_3$, and $AlPh_3$.

9. The method of claim 8, wherein the compound of formula (I) is $AlEt_3$.

10. The method of claim 1, wherein the compound of formula (II) is selected from the group consisting of $Zr(OMe)_n@SiO_2$—$Al_2O_3$, $Zr(OEt)_n@SiO_2$—$Al_2O_3$, $Zr(OnPr)_n@SiO_2$—$Al_2O_3$, $Zr(OiPr)_n@SiO_2$—$Al_2O_3$, $Zr(OnBu)_n@SiO_2$—$Al_2O_3$, $Zr(OCH_2CHMe_2)_n@SiO_2$—$Al_2O_3$, and $Zr(OtBu)_n@SiO_2$—$Al_2O_3$.

11. The method of claim 8, wherein the compound of formula (II) is $Zr(OtBu)_3@SiO_2$—$Al_2O_3$.

12. The method of claim 8, wherein the compound of formula (II) is $Zr(OtBu)_2@SiO_2$—$Al_2O_3$.

13. The method of claim 1, wherein the one or more hydrocarbons is selected from the group consisting of methane, one or more $C_2$-$C_{30}$ hydrocarbons, one or more $C_{31}$-$C_{100}$ hydrocarbons, one or more $C_{101}$-$C_{150}$ hydrocarbons, one or more $C_{150}$-$C_{200}$ hydrocarbons, high density polyethylene (HDPE), low density polyethylene (LDPE), polyethylene (PE), polypropylene, high molecular weight isotactic polypropylene (iPP), linear low density polyethylene (LLDPE), polyethylene-polypropylene-copolymers polystyrene (PS), polystyrene 1000 (PS 1000), polyalphaolefin-10, polyalphaolefins, hydrocarbon oils, hydrocarbon waxes, paraffin wax, mineral oils, synthetic oils, and mixtures thereof.

14. The method of claim 13, wherein the one or more $C_2$-$C_{30}$ hydrocarbons is selected from the group consisting of dodecane, eicosane, and mixtures thereof.

15. The method of claim 13, wherein the one or more hydrocarbons is high density polyethylene (HDPE).

16. The method of claim 1, wherein the step of contacting the complex with one or more hydrocarbons under conditions effective to functionalize the one or more hydrocarbons is carried out by:

adding an electrophile to the reaction mixture to form a functional group on one or more primary carbons of the one or more hydrocarbons.

17. The method of claim 16, wherein the electrophile is selected from the group consisting of $O_2$, $CO_2$, electrophilic halogen, diethyl azodicarboxylate, n-chlorosuccinimide, n-bromosuccinimide, n-iodosuccinimide, ICl, pyridine N-oxide, $H_2O_2$, organic peroxides, and a combination thereof.

18. The method of claim 16, wherein the functional group is selected from the group consisting of alcohol, carboxylic acid, halide, alkyl aluminum, aryl aluminum, and a combination thereof.

19. The method of claim 1, wherein the step of contacting the complex with one or more hydrocarbons under conditions effective to functionalize the one or more hydrocarbons further comprises:

carrying out catalytic chain growth of the one or more hydrocarbons in the presence of olefins.

20. The method of claim 1, wherein the step of contacting the complex with one or more hydrocarbons under conditions effective to functionalize the one or more hydrocarbons further comprises:

carrying out an organometal-catalyzed cross-coupling reaction.

21. The method of claim 1, wherein the step of contacting the complex with one or more hydrocarbons under conditions effective to functionalize the one or more hydrocarbons is carried out at temperature of about 50° C. to about 250° C.

22. The method of claim 21, wherein said temperature is about 150° C.

23. A system comprising:

a compound of formula (I):

$$Al(R^1)_3 \quad\quad\quad\quad (I); and$$

a compound of formula (II):

$$Met(R^2)_n@support \quad\quad\quad\quad (II),$$

wherein $R^1$ is independently selected at each occurrence thereof from the group consisting of $C_6$-$C_{10}$ aryl and $C_1$-$C_{10}$ alkyl;

Met is selected from zirconium, titanium, hafnium, scandium, yttrium, lanthanum and lutetium;

$R^2$ is $C_1$-$C_4$ alkoxy;

n is 1, 2, 3, or 4; and support is alumina or silica/alumina;

wherein the compound of formula (I) and the compound of formula (II) are capable of forming a complex which, when contacted with one or more hydrocarbons under reaction conditions, is effective to functionalize the one or more hydrocarbons, with the proviso that $R^1$ is a group that does not produce a hydride under the reaction conditions.

24. The system of claim 23, wherein $R^1$ is independently selected at each occurrence thereof from the group consisting of methyl, ethyl, n-propyl, n-butyl, t-butyl, n-pentyl, n-octyl, and phenyl.

25. The system of claim 23, wherein the compound of formula (I) is selected from the group consisting of $AlMe_3$, $AlEt_3$, $AliBu_3$, and $AlPh_3$.

26. The system of claim 23, wherein the compound of formula (II) is selected from the group consisting of $Zr(OMe)_n@SiO_2$—$Al_2O_3$, $Zr(OEt)_n@SiO_2$—$Al_2O_3$, $Zr(OnPr)_n@SiO_2$—$Al_2O_3$, $Zr(OiPr)_n@SiO_2$—$Al_2O_3$, $Zr(OnBu)_n@SiO_2$—$Al_2O_3$, $Zr(OCH_2CHMe_2)_n@SiO_2$—$Al_2O_3$, and $Zr(OtBu)_n@SiO_2$—$Al_2O_3$.

27. The system of claim 23, wherein the support is silica/alumina.

* * * * *